United States Patent [19]

Combaz

[11] 3,941,567

[45] Mar. 2, 1976

[54] DEVICE FOR THE ANALYSIS OF MICROSCOPIC OBJECTS BY LASER PYROLYSIS AND CHROMATOGRAPHY IN THE GASEOUS PHASE

[75] Inventor: Andre F. Combaz, Paris, France

[73] Assignee: Compagnie Francaise des Petroles, Paris, France

[22] Filed: Dec. 17, 1973

[21] Appl. No.: 425,583

[30] Foreign Application Priority Data
Dec. 21, 1972 France .............................. 72.45690

[52] U.S. Cl. ............... 23/253 PC; 350/95; 356/246
[51] Int. Cl.² G01N 1/28; G01N 31/08; G02B 21/34
[58] Field of Search ...... 23/230 PC, 232 C, 253 PC; 350/93, 95, 319; 195/142; 356/244, 246

[56] References Cited
UNITED STATES PATENTS

| | | | |
|---|---|---|---|
| 3,580,658 | 5/1971 | Swanson | 350/93 |
| 3,584,957 | 6/1971 | Polchlopek et al. | 356/244 X |
| 3,591,461 | 7/1971 | Bazil et al. | 195/142 |

OTHER PUBLICATIONS

*Anal. Chem.,* Vol. 43, pp. 1057–1058, (1971).
*Anal. Chem.,* Vol. 42, pp. 115–117, (1970).

*Primary Examiner*—Morris O. Wolk
*Assistant Examiner*—Timothy W. Hagan
*Attorney, Agent, or Firm*—Sughrue, Rothwell, Mion, Zinn & Macpeak

[57] ABSTRACT

Pyrolysis analysis of a specimen is effected using a microscope; the specimen to be analysed is mounted on the platform of the microscope and the laser is mounted on the microscope such that the beam passes along the optical axis of the microscope, a total reflecting prism in the microscope being movable between a position on the microscope optical axis for observation of the specimen and a position off the optical axis to permit passage of the laser beam.

5 Claims, 6 Drawing Figures

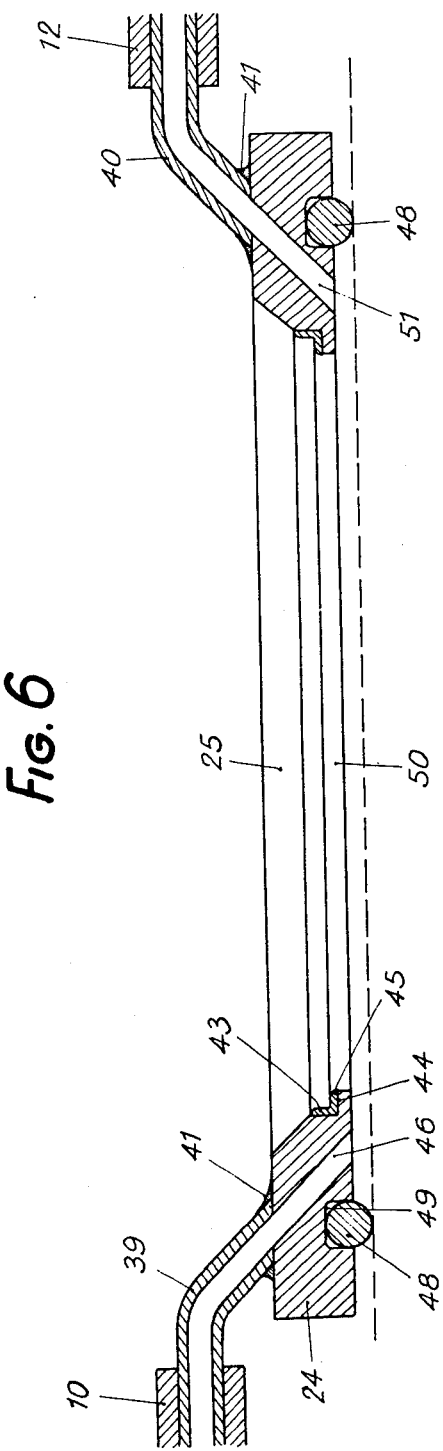

DEVICE FOR THE ANALYSIS OF MICROSCOPIC OBJECTS BY LASER PYROLYSIS AND CHROMATOGRAPHY IN THE GASEOUS PHASE

The invention relates to an apparatus for and a method of analysis by pyrolysis using a laser beam.

Numerous methods for analysing specimens, and in particular hydrocarbons, all based on the use of results obtained by a chromatograph fed with the specimen to be analysed, have already been proposed. Much work has revealed the advantage of a laser beam as a pyrolysis agent, in particular because of the thermal effects obtained and the duration of the pyrolysis. However, none of these methods enabled a microscope to be used simultaneously for direct observation of the specimen and its possible photography and for focussing of the laser beam on a selected microscopic detail of the specimen in order to carry out its analytical pyrolysis.

The use of the microscope associated with a microlaser is known for enucleation of cells for example, but it was not known to use such an association for pyrolysis.

Laser emission has also been used for the elementary analysis of thin sections of metals and minerals with control of the beam by means of a special optical system, a mass spectrograph analysing the pyrolysis products, but if it is desired to study the composition of heterogeneous bodies of complex molecules the advantages offered by the normal use of a microscope are then no longer available, in particular as regards the possibility of examining a microscopic detail and studying its molecular structure by pyrolysis.

According to one aspect of the invention there is provided apparatus for the analysis of a microscopic specimen by pyrolysis, comprising an optical microscope, an ocular tube connecting a micro-laser to the body of the microscope with the axis of the ocular tube coinciding with the optical axis of the microscope, the microscope including a total reflection prism movable between a first position for normal microscopic observation and a second or retraction position for direct passage of a laser beam above the optical axis of the microscope, and means for providing an hermetic chamber on the platform of the microscope and in which pyrolysis is effected, the chamber being connectable to a supply of gas for entraining the pyrolysis products and to a chromatograph.

Thus with use of the above-described apparatus, a quick change may be made from the pyrolysis operation with emission of the laser beam to microscopic observation both in transmitted light and in reflected light, since all that is necessary to do, after emission of the laser beam, is to swivel the total reflection prism of the microscope. The microscopic specimen to be analysed may also be photographed before and after pyrolysis by means of the same microscope.

Furthermore, the hermetic chamber mounted on the platform of the microscope permits intermediate injection into the chromatograph of the pyrolysate resulting from the laser beam falling on the microscopic specimen under investigation, the pyrolysate being conveyed to the chromatograph by a flow of gas. As pyrolysis is carried out on a precisely selected point, all required information on the nature of the analysed specimen may be gathered by the gas chromatograph.

According to another aspect of the invention there is provided a method of analysis by pyrolysis using a laser beam, comprising the steps of introducing the specimen to be analysed into a hermetic chamber connected to a source of gas for entraining the pyrolysate and to a chromatograph, locating a point on the specimen to be analysed by means of a microscope which is coupled to the laser beam producing apparatus, retracting the total reflection prism in the microscope to allow the laser beam to pass along the axis of the microscope, actuating the laser beam producing apparatus, pyrolysate produced in the hermetic chamber being transferred into the chromatograph by the said gas.

The above described method has the advantage of enabling rapid analysis of a specimen and is particularly advantageous when the selected points include organic substances since each of the principal molecular components of all the selected points can then be very rapidly recognized qualitatively and quantitatively instead of carrying out simple elementary analysis.

According to yet another aspect of the invention there is provided a hermetic chamber assembly for use in pyrolysis of a specimen, the assembly comprising a housing open on one face and there provided with a seal, the housing being adapted to bear hermetically either on a slide on which the specimen is mounted or on the surface of a specimen mounted on a slide, and being provided with ports for connection to a source of gas and to a chromatograph, and clamping means for clamping the housing against a slide when on the slide holder platform of a microscope.

As the housing covers the specimen on the slide and the latter is in use rigidly attached to the platform of the microscope, the systematic analysis of the various points on the specimen carried on the slide may easily be effected merely by recording the micrometric displacements of the specimen support relative to the axis of the microscope as well as chromatographic information. Moreover, specimen changing is rapid and easy since it is only necessary to unfasten the clamping means and to change the slide. It will also be noted that the preferred housing is particularly designed to reduce the volume of the hermetic chamber and therefore for the rapid and complete removal of the pyrolysis products, the dilution of which in the scavenging gas is thus reduced to a minimum.

The invention will be more fully understood from the following description of embodiments thereof, given by way of example only, with reference to the accompanying drawings, in which.

Figure 2:
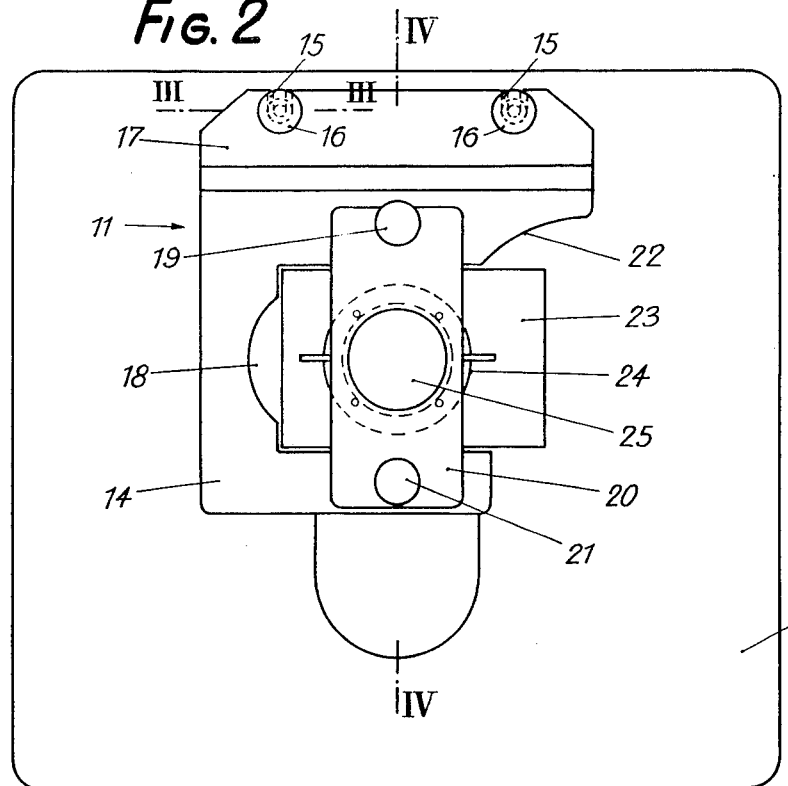
FIG. 2 is the plan of part of the apparatus of FIG. 1.
Figure 3:
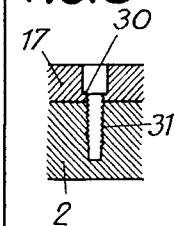
FIG. 3 is the section along the line III—III of FIG. 2.
Figure 4:
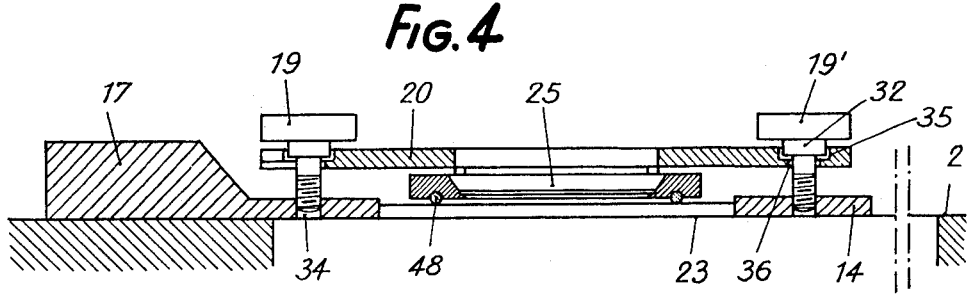
Figure 5:
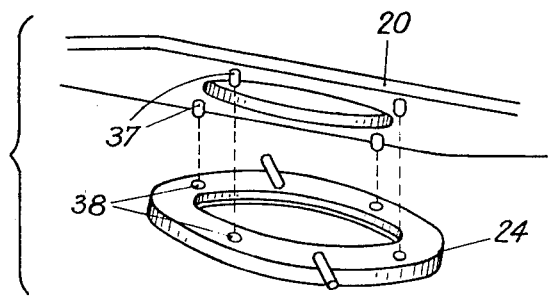

FIG. 4 the section along the line IV—IV of FIG. 2;

FIG. 5 a perspective view of the elements forming a component of the hermetic capacity part of the apparatus shown in FIG. 2; and FIG. 6 an axial section through the component of FIG. 5.

Figure 1:
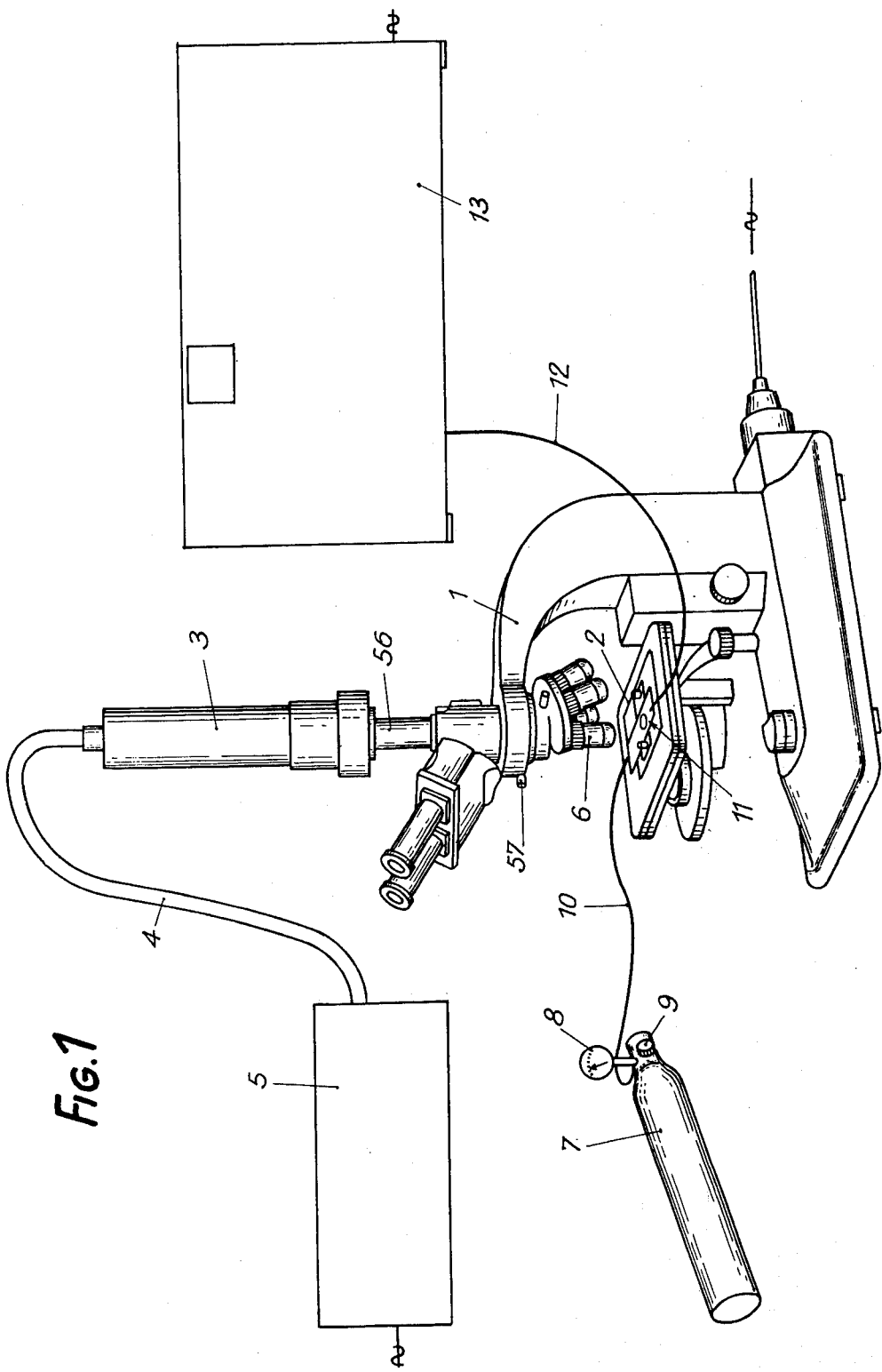
FIG. 1 is a part diagrammatic and part perspective view of an embodiment of apparatus according to the present invention.

The apparatus illustrated in FIG. 1 comprises four principal units, each of which is associated with a micro-collector assembly 11 seated on top of the object-slide 23 fixed to platform 2 of microscope 1.

These four units are the microscope 1, the micro-laser apparatus consisting of supply box 5 and emitter 3 rigidly attached to the microscope 1 by an ocular tube 56, a pressurized helium or nitrogen bottle 7 connected by conduit 10 to micro-collector assembly 11 and a gas chromatograph 13 connected to assembly 11 by conduit 12.

Any microscope provided with an upper opening in the extension of the vertical optical axis may be used, and in particular any photomicroscope of this type.

On platform 2 of the microscope there is provided a slide support 14 (FIGS. 2 to 6) which is provided with two notches 15, in a thickened portion 17 thereof, in which are housed two knurled screws 16. The screws 16 are received in threaded bores 31 in platform 2, a shoulder of each screw 16 bearing on the base 30 of each notch 15 when the screws are tightened to fix the support 14 relative to platform 2.

Beyond thickened portion 17, slide support 14 has a flat U-shape, a slide 23 being received in the U. Insertion and extraction of a slide 23 is facilitated by a cut-out 22 in one arm of the U and by a cut-out 18 in the base of the U.

Slide 23 may be made of glass of standard dimensions, e.g. of 1 to 1.5 mm thickness. The specimen to be analysed may be a thin section of 0.02 to 0.05 mm thickness stuck to the ground glass surface of the slide with araldite. Its upper surface is polished and has no cover-glass. Microscopic observation is then carried out in transmitted light. The specimen may alternatively have a thickness of some millimetres and again be stuck to the slide. Its upper face is polished and the specimen is then observed by reflected light.

A hermetic chamber 50, FIG. 6, is defined laterally by a micro-collector ring 24 positioned above the slide 23 and which is closed centrally by a window 25 transparent to a laser beam. The function of chamber 50 is to collect without loss the pyrolysate produced by impact of the laser beam on the specimen and to permit its scavenging by the gas contained in reservoir 7. The micro-collector ring 24 is preferably a satined stainless steel or brass washer having an outer diameter smaller than that of slide 23 and a height which is just sufficient to permit complete scavenging of the pyrolysate. On the lower face of ring 24 is a groove 49 in which sealing ring 48, e.g. a silicone O-ring with a diameter of 1 mm, is housed. When the O-ring 48 is housed in groove 49 it projects sufficiently therefrom to ensure under pressure the hermeticity of chamber 50 by flattening itself against the walls of the groove 49. O-ring 48 may rest either directly on slide 23 surrounding the specimen, or may rest on the surface of the specimen.

Ports 46 and 51 are provided opposite each other in ring 24 for the supply of helium conveyed by conduit 10 and for the removal of the helium-pyrolysate mixture respectively to and from the chamber 50.

Connectors 39 and 40, the axes of which are in the extension of the axes of ports 46 and 51 are welded to ring 24 at 41 and, for example, after simple bending of these mouthpieces, permit connection thereto of the conduits 10 and 12.

The edge of window 25 forming the upper face of chamber 50 is located in a step 43 in the periphery of the central opening ring 24 and is hermetically stuck to the base 44 thereof by a glue seal 45. The sunken arrangement of window 25, the glass of which is of the order of 0.5 mm thick for example, permits both a reduction of the volume of pyrolysis chamber 50 and the use of more numerous objectives.

To ensure and maintain the hermeticity of chamber 50, the upper surface of ring 24 is formed with small, symmetrically arranged recesses 38 (FIG. 5) in line with the groove 49. As shown, four hemispherical recesses 38, e.g. 0.5 mm deep, are provided to receive four lugs 37 of approximately 1.5 mm length of clamping device 20.

This device 20 in the form of a bridge clamps ring 24 against slide 23 by means of micrometric screws 19. Portions 32 of the screws 19 bear on the bases of steps 35 surrounding orifices 36 passing through plate 20. The ends of the screws 19 are received in threaded bores 34 in the slide support 14.

In the example described, micro-laser apparatus 3 may be a commercial apparatus designed for biological research. The emission head is of the cylindrical ruby monocrystal type. Ocular tube 56, which is of a suitable length, is set on the optical axis of microscope 1. A button 57 is provided for commanding the retraction of the total reflection prism used for normal microscopic observation and which must be withdrawn to allow direct passage of the laser beam along the optical axis of the microscope for the pyrolysis operation.

Perfectly electrically insulated electric lead 4 connects emission head 3 to supply box 5 which can use a current supply of 110 or 120 V and produce a high actuation voltage of 10,000 V by means of a battery of capacitors.

The supply of gas providing a neutral atmosphere in pyrolysis chamber 50 and the transfer of the pyrolysate into the column of chromatograph 3 is controlled by knurled knob 9, a manometer 8 being provided for monitoring the gas pressure. Conduit 10, connecting bottle 7 to connector 39, may be a simple polyvinyl flexible tube.

Gas chromatograph 13 is of any known type having a column selected according to the nature of the products to be detected and the required resolution, an ionization flame detector, a recorder and optionally apparatus for integration and digital conversion of the measurements. The conduit 12 connecting the chamber 50 to the chromatograph 13 is, for example a copper pipe 12 approximately 3 mm in diameter and 1 m long, which may include spirals and be heated to 200°. The flame detector may be of the hydrogen combustion type and the flame may be fed by means of a small air-pump. As chromatographs are widely known, it has only been shown diagrammatically in FIG. 1.

When it is required to analyse a specimen, screws 19 are loosened to enable a slide 23 carrying a specimen to be introduced into slide support 14. Hermeticity of the pyrolysis chamber 50 is then obtained by tightening the micrometric screws 19. The point on the specimen to be analysed is then located by operation of the microscope 1 to displace the slide as is conventional. The reflection prism in the microscope is then retracted by operation of button 57 and emission of the laser beam is started by operation of box 5, after scavenging of pyrolysis chamber 50 with gas from the bottle 7.

By way of example, the duration of the conveyance of the pyrolysis gas, passage through the chromatograph column and its recording is approximately 3 minutes. It will thus be seen that all that is necessary is to automatically control the position change of the slide relative to the optical axis of the microscope at regular intervals of three minutes to carry out a point by point analysis of a specimen and deduce from it an overall statistical analysis of the specimen.

The above-described apparatus is thus applicable both to automatic analysis and to the analysis of a particular point whatever may be the composition of the specimen to be analysed, e.g. rock, coal, etc.

It will also be noted that because of special ocular tube 56 and of the very small height of pyrolysis chamber 50, commercial objectives may be used. Furthermore, very high magnifications may be obtained by retaining these objectives and replacing the eye pieces of the microscope with more powerful eye pieces and then replacing ocular tube 56 of the laser with a suitable ocular tube.

What is claimed is:

1. In an apparatus for the analysis of a microscopic specimen by pyrolysis in a hermetic chamber having, an optical microscope having an optical axis, a total reflection prism movable between a first position on said optical axis for normal microscopic observation, and a second retracted position off said optical axis, and a platform on which a specimen will be mounted;

a micro-laser;

an ocular tube having an axis;

means for mounting said ocular tube on said microscope with said axis of said ocular tube coincident with said optical axis of said microscope;

means for mounting said micro-laser on said ocular tube so that a beam from said laser will be directed along said axes onto said specimen;

means for connecting said chamber to a supply of gas for entrainment of pyrolysis products;

a gas chromatograph;

means for connecting said gas chromatograph to said chamber;

the improvement comprising;

means providing the hermetic chamber being disposed on said microscope platform for receiving a specimen and in which pyrolysis thereof will occur, said means providing said hermetic chamber including a slide defining the lower surface onto which said specimen is placed, means defining side walls of said chamber, sealing means between said slide and said means defining side walls and a window forming the top of said chamber; and means to clamp said hermetic chamber to said platform, said clamping means being arranged to allow movement of said slide relative to said platform.

2. Apparatus as claimed in claim 1, wherein said hermetic chamber means comprises a ring bearing an annular groove in its lower surface for receiving said sealing means, said window hermetically affixed in its upper portion, and two ports connectable respectively to a gas supply and a chromatograph, said sealing means being pressed on a slide by a bearing plate carrying lugs aligned with said sealing means, said lugs engaging in recesses in said ring, micrometic screws holding said ring against said slide while engaging in threaded bores provided in means carrying said slide and attached to said platform of said microscope.

3. Apparatus as claimed in claim 1, wherein said sealing means is clamped between said slide and a ring by said clamping means comprising, a bridge bearing on said ring, said bridge being mounted by micrometric screws engaging in threaded bores in said hermetic chamber means.

4. Apparatus as claimed in claim 3, wherein said bridge bears on said ring at points aligned with said sealing means.

5. In an apparatus for the analysis of a microscopic specimen by pyrolysis in a hermetic chamber having, an optical microscope having an optical axis, a total reflection prism movable between a first position on said optical axis for normal microscopic observation and a second retracted position off said optical axis, and a platform on which a specimen will be mounted;

a micro-laser;

an ocular tube having an axis;

means for mounting said ocular tube on said microscope with said axis of said ocular tube coincident with said optical axis of said microscope;

means for mounting said micro-laser on said ocular tube so that a beam from said laser will be directed along said axes onto said specimen;

means for connecting the hermetic chamber to a supply of gas for entrainment of pyrolysis products;

a gas chromatograph;

means for connecting said gas chromatograph to said chamber;

the improvement comprising;

means providing the hermetic chamber being disposed on said microscope platform in which pyrolysis thereof will occur, said means providing a hermetic chamber including a window forming the top of said chamber, means defining side walls of said chamber, the surface of the specimen to be analyzed defining the lower surface of said chamber and sealing means between said means defining side walls and said specimen; and means to clamp said hermetic chamber to said platform.

* * * * *